United States Patent [19]

Halle et al.

[11] 4,161,485
[45] Jul. 17, 1979

[54] CYCLIC SILYL PEROXIDES

[75] Inventors: Reidar Halle, Novato; Lawrence A. Bock, Walnut Creek, both of Calif.

[73] Assignee: Argus Chemical Corporation, Brooklyn, N.Y.

[21] Appl. No.: 914,817

[22] Filed: Jun. 12, 1978

[51] Int. Cl.² ............................................. C07F 7/08
[52] U.S. Cl. ........................ 260/448.2 R; 260/448.2 E
[58] Field of Search ................. 260/448.2 R, 448.2 E

[56] References Cited

U.S. PATENT DOCUMENTS

| | | | |
|---|---|---|---|
| 3,338,864 | 8/1967 | Mageli et al. | 260/45.7 |
| 3,700,712 | 10/1972 | Ostrozynski | 260/448.2 E |
| 3,856,606 | 12/1974 | Fan et al. | 156/329 |

OTHER PUBLICATIONS

Fan et al., "Rubber World", 6/71, pp. 56–62.
Bazant et al., "Organosilicon Compounds", vol. 2, part 1, Academic Press, N.Y. (1965), p. 410.

*Primary Examiner*—Paul F. Shaver
*Attorney, Agent, or Firm*—Townsend and Townsend

[57] ABSTRACT

Novel cyclic silylperoxides in which a silicon atom directly bonded to at least two peroxy oxygen atoms in a ring of from 8 to 11 atoms are useful as agents for crosslinking high density polyethylene and/or as catalysts for curing unsaturated polyester resins.

21 Claims, No Drawings

CYCLIC SILYL PEROXIDES

This invention relates to novel silicon peroxides, the processes by which they are made and to their uses. More particularly, this invention relates to novel cyclic silyl compounds in which a silicon atom is directly bonded to two peroxide oxygen atoms and which are characterized by the following formula:

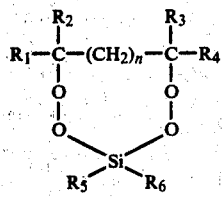

wherein n is an integer from 1 to 4; $R_1$, $R_2$, $R_3$ and $R_4$ are each selected from the group consisting of lower alkyl and are preferably of 1 to 3 carbon atoms; $R_5$ is selected from the group consisting of alkyl, alkenyl, and aryl; and $R_6$ is selected from the group consisting of alkyl, alkenyl and aryl. $R_5$ and $R_6$ preferably each have from 1 to 10 carbon atoms.

Linear silicon peroxides are known for their utility as crosslinking agents for high density polyethylene (HDPE) and/or as catalysts for curing polyester resins. Linear silyl peroxides have also been employed as coupling agents for bonding organic polymers to both organic and inorganic substrates.

Heretofore, it was known that linear silyl peroxides could be prepared generally by several methods. The classical manner for preparing linear silyl peroxides involved the reaction of a halogen-silicon compound with a peroxide compound in the presence of an amine base. Similarly, the art teaches that peroxysilanes can be prepared by reacting a hydroaminosilane with a peroxide as shown by Pike and Shaffer, "Chemical Abstracts", Vol. 52, page 4471g (1958). The art also now teaches that peroxysilanes can be prepared by reacting a dimethylaminosilicon compound with a peroxide as disclosed in U.S. Pat. No. 3,700,712.

More particularly, the art which developed in regard to the preparation of various silyl peroxide compounds teaches that where dihydroperoxides are reacted with either hydroaminosilanes or with dihalogen-silicon compounds in the presence of an amine base the resulting silyl peroxides will be linear. For example, U.S. Pat. No. 3,700,712 teaches that silicon compounds having the formula $R_2 Si[N(CH_3)_2]_2$ wherein R is hydrogen, methyl, ethyl, vinyl, allyl or phenyl radicals when reacted with organic hydroperoxide compounds containing two hydroperoxy groups will produce linear silicon peroxides having the following formula: $R_2 Si[OO\text{-}R']_2$ wherein R' is a hydrocarbon radical, the remainder of the organic hydroperoxide starting material. Further, U.S. Pat. No. 3,856,606 teaches that the reaction of silicon halides and dihydroperoxides having the formula HOOR'OOH in the presence of amine compounds will yield silicon peroxides wherein the number of silicon atoms is equivalent to the number of hydroperoxy groups substituted on R'.

Accordingly it is a general object of this invention to provide a novel group of silyl peroxide compounds that are cyclic in structure and have utility as catalysts for curing unsaturated polyester resins and/or as crosslinking agents of high density polyethylenes.

Other objects and advantages of the present invention will become apparent in the course of the following discussion, and as such are intended to be objects thereof, whether enumerated or not.

SUMMARY OF THE INVENTION

It has been discovered that cyclic silyl peroxides can be prepared by reacting certain silane compounds with selected dihydroperoxides. More particularly, heretofore unknown cyclic silyl peroxides having the formula:

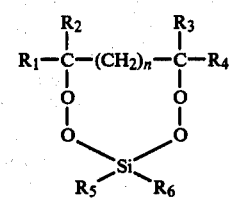

have been prepared by reacting dihydroperoxides having the formula:

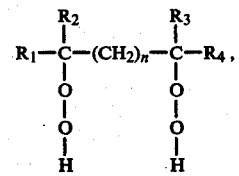

wherein $R_1$, $R_2$, $R_3$, $R_4$ and n are as described above; with silicon compounds having the formula $R_5R_6SiX_2$, wherein X is selected from the group consisting of halogen and $N(CH_3)_2$ and $R_5$ and $R_6$ are as described above, except when X is halogen said reaction taking place in the presence of ammonia or other amine base.

DESCRIPTION OF THE PREFERRED EMBODIMENTS

The term dihydroperoxides as defined herein refers to compounds having the formula

$R_1R_2COOH(CH_2)_nCOOH R_3R_4$ wherein $R_1$, $R_2$, $R_3$, $R_4$ and n are as defined above. The preferred hydroperoxides empolyable in this invention are those wherein $R_1$, $R_2$, $R_3$ and $R_4$ are lower alkyls having from 1 to 3 carbon atoms, especially methyl, and n is 2. Illustrative of useful dihydroperoxides are 2,5-dimethyl-2,5-dihydroperoxy hexane and 3,6-dimethyl-3,6-dihydroperoxyoctane.

The usable silicon halides in this invention broadly speaking include any silicon containing compound wherein at least two halogen atoms are directly bonded to the silicon atom. Preferred silicon halides are those in which there is an even number of halogen atoms directly bonded to the silicon atom. The remaining valences of the silicon atom, that is, those valences which are not taken up by halogen, may be bonded to any alkyl, alkenyl or aryl group. Illustrative of such employable silicon halide compounds are the following: dichloro dimethylsilane; dichloro methyl phenylsilane; dichloro methyl vinyl silane; dichlorodiethyl silane; and dichloro methyl n-amyl silane.

Specific examples of preferred dimethyl amino silicon compounds are $Me_2Si(NMe_2)_2$; $ViMeSi(NMe_2)_2$ and the like, wherein Me represents a methyl radical (—CH₃) and Vi represents a vinyl radical (—CH=CH₂).

When the cyclic silyl peroxides of this invention are prepared using a silicon-halide as an initial reactant, the reaction should be carried out in the presence of ammonia or any other amine base. Typical amine bases useable are trimethylamine, triethylamine and pyridine.

The manner and order in which the reaction components are mixed is not critical. In general, the organic hydroperoxide is placed in a suitable reaction vessel and the silicon halide or silicon-nitrogen compound is added, preferably with moderate agitation. It is desirable to effect good mixing between the reactants so as to insure complete reaction, but this is not critical. To some extent it may affect the yield or reaction rate.

When a silicon halide is employed, the mixture is generally cooled prior to introducing the ammonia gas or other amine base. When a silicon-nitrogen compound is employed as an initial reactant the reaction mass may be heated to initiate the reaction. The formation of cyclic silyl peroxides involves exothermic reactions. Accordingly, during the reaction the temperature may rise as a result thereof. Generally it is desirable to maintain the temperature of the reaction at the levels at which the most favorable results are achieved. This is within the skill of the operator in the manufacture of a given cyclic silyl peroxide and heat withdrawal methods such as conduction, radiant, or convection cooling may be employed in order to effect a measure of control over the process. Similarly, temperature may be affected by varying the rate at which the reactants are added together. Preferably, the temperature at which the reactions are effected may range from a temperature below 0° C. at which temperature the silicon halide has some solubility in the solvent employed to a maximum temperature above 0° C. limited, of course, by the decomposition temperature of the dihydroperoxide or the boiling of any reactant or solvent. Most preferably the reactions are carried out at −20° C. to 60° C. and usually at 5°–10° C.

In view of the reactivity of the silicon-containing reactants towards hydroxylated substances, it is preferred that the reaction be conducted in the absence of a hydroxylated substance, e.g., water or alcohols.

Solvents, while not necessary, can be used if desired for the purpose of dehydrating and/or dissolving the organic hydroperoxide. Useable solvents in the practice of this invention are those in which the silicon halide and dihydroperoxide are soluble. Also it is desirable that the solvent should be one which does not interfere with the reaction. Therefore, it is typically desirable not to employ a highly polar solvent. However, slightly polar solvents, such as ethers, are employable. Because the dihydroperoxides employed in this invention are not very soluble in non-polar solvents, such as in hexane, the slightly polar solvents are, in fact, preferred over the non-polar liquid hydrocarbons typically found most useful in the preparation of linear silyl peroxides such as those described in U.S. Pat. No. 3,856,606.

The molar amount of dihydroperoxide employed is desirably equivalent to the molar amount of silicon dihalide or silicon dimethyl amino compound. While amounts that are less or in excess of said stoichiometric ratio may be used if desired, the yields of cyclic silyl peroxides may be affected.

There is described hereinafter a number of examples for the purpose of illustrating and as such are not to be considered as limitative. A number of useful techniques for using the silyl peroxides are described in addition to the method of their preparations.

EXAMPLE 1

Into a one liter flask equipped with a motorized stirrer is added 0.15 mole (25.17g, 98.47% pure) of 2,5-dimethyl-2,5-dihydroperoxyhexane and 0.15 mole (19.35g) of dichlorodimethylsilane in 400 ml of anhydrous ether. This mixture is cooled to about 5° C., and ammonia gas is introduced cautiously. Reaction temperature is maintained between 5° and 10° C. by use of an ice bath and by adjusting the rate of gas introduction. Ammonia addition is continued for 30 to 40 minutes until the exothermic reaction has stopped. The reaction mixture is then stirred at room temperature for an additional 3 hours. The salts are removed by filtration and the ether is removed by distillation. The crude yield of a colorless solid was 26.7 grams. To purify the crude product hexane is added and the mixture is filtered to remove a small amount of insoluble, unreacted 2,5-dimethyl-2,5-dihydroperoxyhexane. Evaporation of the hexane yields 21.9 grams (62.4%) of 3,3,6,6,9,9-hexamethyl-1,2,4,5-tetraoxa-3-silacyclononane having a melting point of 44.5°–48° C. The product is 95.5% pure based upon active oxygen (A.O.) analysis wherein theoretical A.O. is 13.67% and A.O. found is 13.05%. Analysis of the product supports the structure

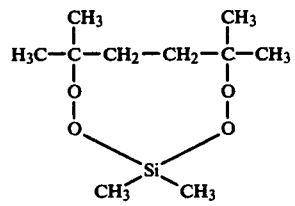

as follows: (1) I.R. spectrum indicates no terminal hydroperoxy (—OOH) groups; (2) the molecular weight corresponds to a cyclic structure; and (3) various chromatographic analyses verify a very non-polar species.

EXAMPLE 2

Into a 250 ml flask equipped with a magnetic stirring bar, addition funnel and calcium sulfate drying tube is placed a solution of 10.84g (0.06 mole, 98.66% pure) of 2,5-dimethyl-2,5-dihydroperoxyhexane in 120 ml of anhydrous ether. The solution is cooled to 16° C. and a solution of 8.77g (0.06 mole) of bis(dimethylamino) dimethylsilane in 30 ml of anhydrous ether is added slowly dropwise. The reaction temperature is maintained between 15° and 20° by use of an ice bath and by adjusting the rate of addition. After the addition is complete, the solution is stirred at room temperature for one hour. The solution is filtered to remove a small amount of suspended solid. The solvent is removed by distillation yielding 13.75g of 3,3,6,6,9,9-hexamethyl-1,2,4,5-tetraoxa-3-silacyclononane (theoretical yield 14.05g, 97.9%; A.O. analysis 13.32%, theoretical 13.67%, 97.4% pure). The infrared spectrum of the reaction product of this example is identical to the spectrum of material produced in Example 1.

EXAMPLES 3–6

A series of cyclic silyl peroxide compounds were prepared by varying the silyl dichloride reactant of Example 1 and otherwise following the procedure set forth therein, except that the crude products were usually purified by silica gel chromatography. The mole ratio of dihydroperoxide and silyl dichloride continued to be 1:1. The silyl dichlorides employed and the products formed are shown in Table I.

Table I

| Example | Silyl Dichloride | Product | % Purity by A.O. analysis |
|---------|------------------|---------|---------------------------|
| 3. | dichloromethyl-phenyl silane | 3-phenyl-3,6,6,9,9-pentamethyl-1,2,4,5-tetraoxa-3-silacyclononane | 81.7 |
| 4. | dichloromethyl vinyl silane | 3-vinyl-3,6,6,9,9-pentamethyl-1,2,4,5-tetraoxa-3-silacyclononane | 94.3 |
| 5. | dichlorodiethyl silane | 3,3-diethyl-6,6,9,9-tetramethyl-1,2,4,5-tetraoxa-3-silacyclononane | 90.2 |
| 6. | dichloromethyl n-amyl silane | 3-n-amyl-3,6,6,9,9-pentamethyl-1,2,4,5-tetraoxa-3-silacyclononane | 94.8 |

EXAMPLE 7

The procedure of Example 1 was repeated except that 0.15 moles of 3,6-dimethyl-3,6-dihydroperoxy octane was employed in place of the 2,5-dimethyl-2,5-dihydroperoxy hexane. The crude 3,3,6,9-tetramethyl-6,9-diethyl-1,2,4,5-tetraoxa-3-silacyclononane was chromatographed on silica gel to give a final product of 93.0% purity.

EXAMPLES 8–9 — CROSSLINKING TEST PROCEDURE

The desired amount of peroxide is dissolved in n-hexane and added to 30.00g of HDPE powder (Rhone-Poulene Manolene ER63ONS) dispersed in about 100 ml hexane in a round bottom flask. After mixing, the solvent was removed under reduced pressure using a rotating evaporator and a 40° C. water bath. Platen temperatures on the press are adjusted until a surface pyrometer indicates the desired temperature. A properly shaped sheet of aluminum foil is placed on the lower platen and the press is closed. As soon as the ram pressure gauge moves from the "zero" reading the press is released. The dry blended resin is then evenly distributed over the aluminum "shell" in the lower platen and covered with a second piece of foil. The press is closed and the press time begins when the ram pressure gauge maintains 1000 psig. At the end of the cure cycle, the aluminum coated tray is removed and quickly cooled in a water bath. Finally, the coating is removed by immersion in about 36% hydrochloric acid.

To determine the % wt gel, approximately 0.30g of tray are removed and cut into small pieces. These pieces are placed in a stainless steel, 100 mesh screen pouch and extracted in 2 liters of boiling xylene containing 10 grams of Plastanox 2246 anti-oxidant. After about 16 hours the pouches are removed and dried overnight in a 150° C. vacuum oven at approximately 2mm Hg.

The percent weight gel is calculated by the following formula:

$$\% \text{ wt gel} = \frac{W_1 - (W_2 - W_3) - B \times 100}{W_1}$$

where:
$W_1$ = wt of sample, g
$W_2$ = wt of sample and pouch, g
$W_3$ = wt of sample and pouch after extraction, g
B = blank value for resin without peroxide.

Table II

| | | % Gel | | | |
|---|---|---|---|---|---|
| Cyclic Silyl Peroxide | Temp. °C. | 200 | 240 | 280 | 310 |
| None - Blank | | — | 0.8 | 0.6 | — |
| 3,3,6,6,9,9-hexamethyl-1,2,4,5-tetraoxa-3-silacyclononane | | <1 | 87.1 | 83.7 | 84.6 |
| 3,3,6,9-tetramethyl-6,9-diethyl-1,2,4,5-tetraoxa-3-silacyclononane | | — | 1 | 88.9 | — |

EXAMPLE 10 — CURING POLYESTER RESINS

Data on the testing of these new cyclic silyl peroxides for curing of ethylenically unsaturated polyester resins are found in Table III. The listed results are average values from duplicate runs in a Hot Block Gel Tester. The tests were carried out with zero time at 270° F. The polyester resin used was W. R. Grace-Hatco Div GR 14010. Sample size was 5cc of resin with 1% cyclic silyl peroxide catalyst.

Table III

| Peroxide | Gel Time, Min. | Exotherm Time, Min. | Peak Temp., F.° |
|----------|----------------|---------------------|------------------|
| 3,3,6,6,9,9-hexamethyl-1,2,4,5-tetraoxa-3-silacyclononane | 6.22 | 8.70 | 332 |
| 3-phenyl-3,6,6,9,9-pentamethyl-1,2,4,5-tetraoxa-3-silacyclononane | 4.74 | 6.64 | 362 |
| 3-vinyl-3,6,6,9,9-pentamethyl-1,2,4,5-tetraoxa-3-silacyclononane | 4.53 | 6.71 | 367 |
| 3,3-diethyl-6,6,9,9-tetramethyl-1,2,4,5-tetraoxa-3-silacyclononane | 8.87 | 12.69 | 290 |
| 3-n-amyl-3,6,6,9,9-pentamethyl-1,2,4,5-tetraoxa-3-silacyclononane | 8.63 | 12.98 | 287.5 |
| 3,3,6,9-tetramethyl-6,9-diethyl-1,2,4,5-tetraoxa-3-silacyclononane | 6.09 | 8.58 | 321 |

What is claimed is:

1. A cyclic silyl peroxide having the formula

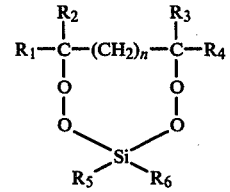

wherein
$R_1$, $R_2$, $R_3$ and $R_4$ are selected from the group consisting of lower alkyl having from 1 to 3 carbon atoms;
$R_5$ and $R_6$ are each selected from the group consisting of alkyl, alkenyl and aryl; and
n is an integer from 1 to 4.

2. A silyl peroxide as described in claim 1 wherein $R_1$, $R_2$, $R_3$, $R_4$ are lower alkyls having from 1 to 3 carbon atoms and n is 2.

3. A silyl peroxide as described in claim 2 wherein $R_5$ is alkyl having from 1 to 10 carbon atoms.

4. A silyl peroxide as described in claim 3 wherein $R_6$ is selected from the group consisting of n-amyl, vinyl and phenyl.

5. A silyl peroxide as described in claim 3 wherein $R_6$ is alkyl having from 1 to 10 carbon atoms.

6. A silyl peroxide as described in claim 2 wherein $R_1$, $R_2$, $R_3$ and $R_4$ are methyl.

7. A silyl peroxide as described in claim 6 wherein $R_5$ and $R_6$ are methyl.

8. A silyl peroxide as described in claim 6 wherein $R_5$ is methyl and $R_6$ is phenyl.

9. 3-vinyl-3,6,6,9,9-pentamethyl-1,2,4,5-tetraoxa-3-silacyclononane.

10. 3,3-diethyl-6,6,9,9-tetramethyl-1,2,4,5-tetraoxa-3-silacyclononane.

11. 3-n-amyl-3,6,6,9,9-pentamethyl-1,2,4,5-tetraoxa-3-silacyclononane.

12. A silyl peroxide as described in claim 1 wherein $R_1$ and $R_4$ are ethyl; $R_2$, $R_3$, $R_5$ and $R_6$ are methyl and n is 2.

13. A process for preparing cyclic silyl peroxides as defined in claim 1 comprising reacting a dihydroperoxide having the formula

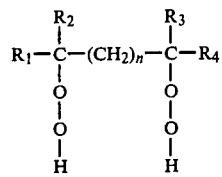

with a silane having the formula $R_5R_6SiX_2$
wherein $R_1$, $R_2$, $R_3$ and $R_4$ are each selected from the group consisting of lower alkyl; $R_5$ and $R_6$ are each selected from the group consisting of alkyl, alkenyl and aryl; n is an integer from 1 to 4; and X is selected from the group consisting of halogen and dimethyl amino.

14. A process as described in claim 13 wherein X is halogen and said reaction is carried out in the presence of ammonia or other amine base at a temperature of $-20°$ to $60°$ C.

15. A process as described in claim 14 wherein n is 2, $R_1$, $R_2$, $R_3$ and $R_4$ are each lower alkyl having from 1 to 3 carbon atoms, and $R_5$ and $R_6$ are each alkyl having from 1 to 10 carbon atoms.

16. A process as described in claim 15 wherein $R_1$ and $R_4$ are selected from the group consisting of methyl and ethyl and $R_2$, $R_3$, $R_5$ and $R_6$ are each methyl.

17. A process as described in claim 14 wherein X is chlorine and said reaction is carried out in the presence of ammonia at a temperature of from $0°$ to $25°$ C.

18. A process for preparing cyclic silyl peroxides comprising reacting a dihydroperoxide and a dimethylaminosilane having the formula: $R_5R_6Si[N(CH_3)_2]_2$ wherein $R_5$ and $R_6$ are each selected from the group consisting of alkyl, alkenyl and aryl.

19. A process as defined in claim 18 wherein $R_5$ and $R_6$ are alkyl having from 1 to 10 carbon atoms.

20. A process in accordance with claim 13 or 18 wherein the reaction is carried out in a slightly polar solvent.

21. A process in accordance with claim 20 wherein said slightly polar solvent is anhydrous ether.

* * * * *